United States Patent

Aihara et al.

(10) Patent No.: US 7,482,445 B2
(45) Date of Patent: Jan. 27, 2009

(54) CRYSTALLINE CARBAPENEM INTERMEDIATE

(75) Inventors: Kazuhiro Aihara, Kanagawa-Ken (JP); Toshifumi Hasegawa, Kanagawa-Ken (JP); Shinichi Kitahara, Kanagawa-Ken (JP); Takashi Watanabe, Kanagawa-Ken (JP); Takashi Ando, Kanagawa-Ken (JP); Takehiko Sawabe, Kanagawa-Ken (JP); Eiki Shitara, Kanagawa-Ken (JP); Kunio Atsumi, Kanagawa-Ken (JP); Kazumi Ota, Kanagawa-Ken (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 423 days.

(21) Appl. No.: 10/561,200

(22) PCT Filed: Jun. 18, 2004

(86) PCT No.: PCT/JP2004/008625

§ 371 (c)(1),
(2), (4) Date: Dec. 19, 2005

(87) PCT Pub. No.: WO2004/113356

PCT Pub. Date: Dec. 29, 2004

(65) Prior Publication Data

US 2007/0167620 A1 Jul. 19, 2007

(30) Foreign Application Priority Data

Jun. 18, 2003 (JP) ............................. 2003-172723

(51) Int. Cl.
   *C07F 9/568* (2006.01)
(52) U.S. Cl. .................................... 540/200
(58) Field of Classification Search ....................... None
   See application file for complete search history.

(56) References Cited

U.S. PATENT DOCUMENTS 5,990,101 A 11/1999 Aihara et al.
6,825,187 B2 * 11/2004 Kano et al. ............ 514/210.09

FOREIGN PATENT DOCUMENTS

WO 96/28455 9/1996
WO 01/53305 7/2001

OTHER PUBLICATIONS

Susan M. Schmitt et al., "The Synthesis of 2-(Functionalized Methyl)- 1β-Methylcarbapenems", The Journal of Antibiotics, Jun. 1988, pp. 780-787.
Ravindra Nath Guthikonda et al., "Structure-Activity Relatinoships in the 2-Arylcarbapenem Series: Synthesis of 1-Methyl-2-arylcarbapenems", J. Med. Chem. 1987, pp. 871-880, vol. 30.

* cited by examiner

*Primary Examiner*—Mark L Berch
(74) *Attorney, Agent, or Firm*—Wenderoth, Lind & Ponack, L.L.P.

(57) ABSTRACT

This invention relates to crystals of compounds of formula (I), wherein TBS represents t-butyldimethylsilyl, and Ph represents phenyl, or its salt or solvate. Compounds of formula (I) are synthesis intermediates of 2-substituted-1β-methyl carbapenem compounds useful as antimicrobial agents. The crystals of the present invention have excellent handleability and can realize the production of carbapenem compounds having excellent antimicrobial activity in a simpler manner with improved yield and purity.

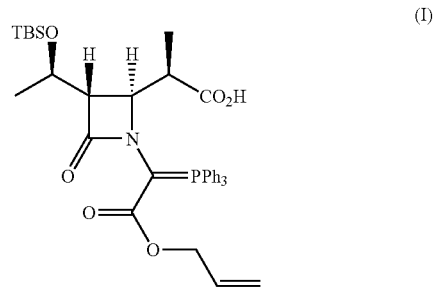

(I)

21 Claims, No Drawings

CRYSTALLINE CARBAPENEM INTERMEDIATE

This application is a national stage of PCT/JP2004/008625 filed Jun. 18, 2004. The entire contents of the above-identified application is hereby incorporated by reference.

BACKGROUND OF THE INVENTION

1. Field of the Invention

The present invention relates to a crystal of a synthetic intermediate of a 2-substituted-1β-methyl carbapenem compound useful as antimicrobial agents.

2. Background Art

2-Substituted-1β-methyl carbapenem compounds are known to be useful as antimicrobial agents. In the derivation of various 2-substituted-1β-methyl carbapenem compounds, compounds of formula (I) are important intermediates therefor.

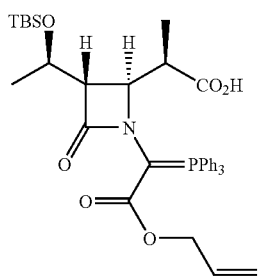

(I)

wherein TBS represents t-butyldimethylsilyl; and Ph represents phenyl.

For example, J. Med. Chem., 30, 871 (1987) describes the synthesis of 2-aryl-1β-methyl carbapenem from the compound of formula (I) (see scheme 1 below). This document reports that the resultant compound has higher antimicrobial activity against *Staphylococcus aureus, Enterococcus, Escherichia coli* and the like than imipenem (IPM) and has higher stability against renal DHP-1 than IPM.

Scheme 1:

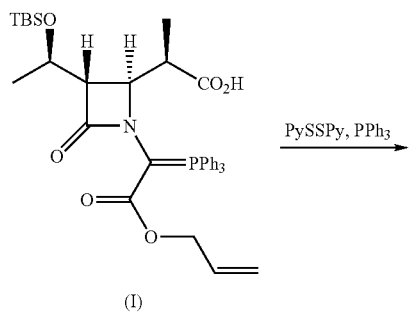

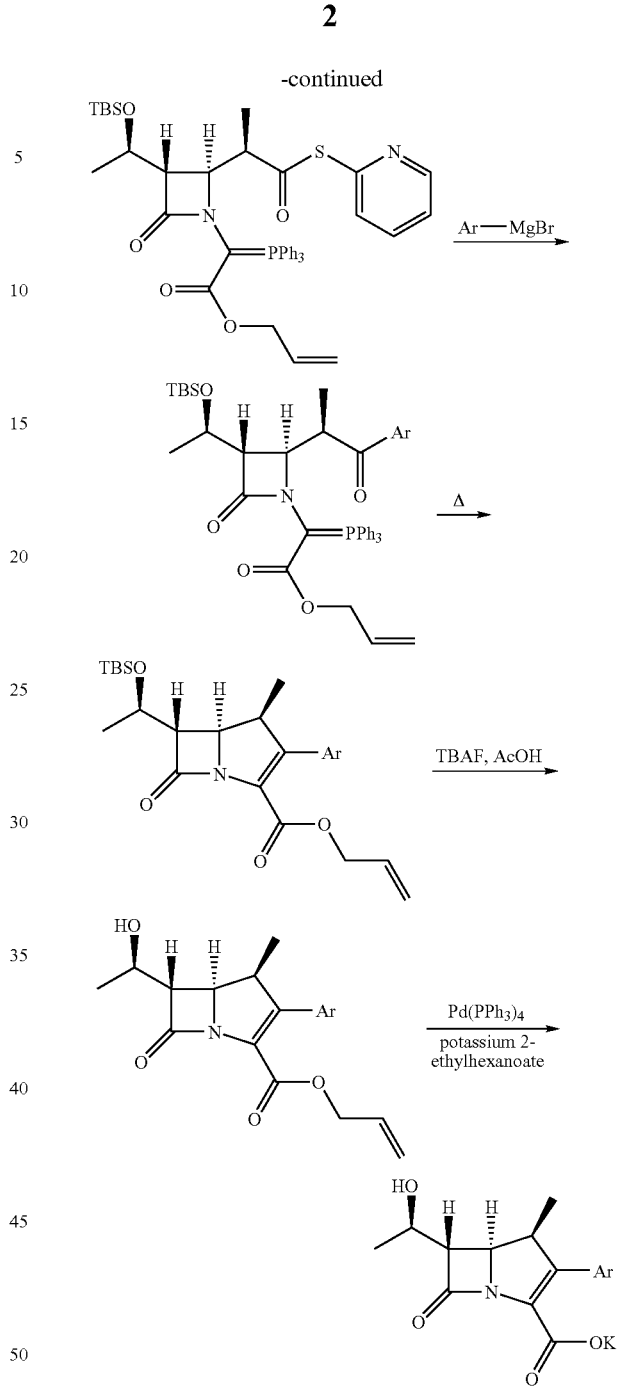

wherein TBS and Ph are as defined above; PySSPy represents 2,2'-dipyridyldisulfide; Ar represents aryl; TBAF represents tetrabutylammonium fluoride; and Ac represents acetyl. The triangular symbol means that heating (for example, 80 to 150° C.) is carried out.

J. Antibiotics, 41, 780 (1988) describes the synthesis of 2-ureido-1β-methyl carbapenem from the compound of formula (I) (see scheme 2 below). This document reports that the resultant compound has higher antimicrobial activity against *Enterococcus, Escherichia coli, Klebsiella pneumoniae* and the like than IPM and has higher stability against renal DHP-1 than IPM.

Scheme 2:

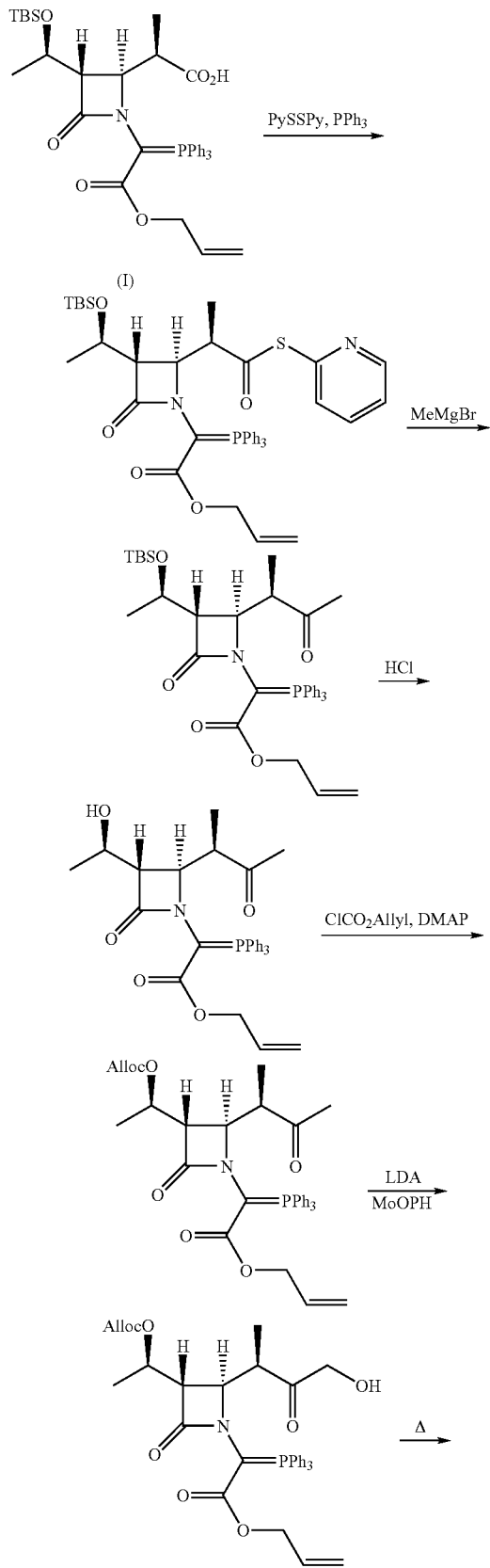

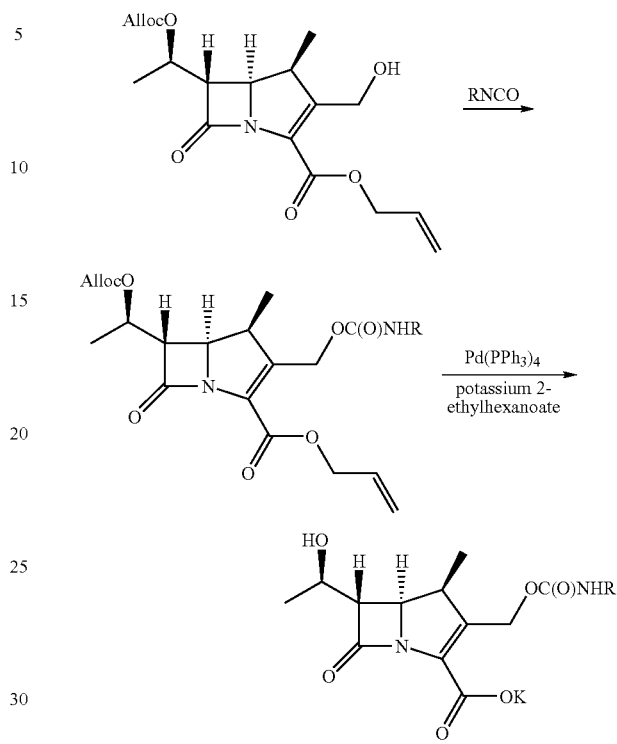

wherein TBS, Ph, and PySSPy are as defined above; DMAP represents 4-N,N-dimethylaminopyridine; LDA represents lithium diisopropylamide; R represents a hydrogen atom, optionally substituted alkyl, phenyl or the like; Me represents methyl; and Alloc represents allyloxycarbonyl. The triangular symbol means that heating (for example, 80 to 150° C.) is carried out.

WO 96/28455 by the present inventors describes the synthesis of 2-imidazo[5,1-b]thiazoliummethyl-1β-methyl carbapenem from the compound of formula (I) (see scheme 3 below). This document reports that the resultant compound has higher antimicrobial activity against *Staphylococcus aureus* including MRSA, *Enterococcus, Escherichia coli*, pneumococci, *Pseudomonas aeruginosa* and the like than IPM and has higher stability against renal DHP-1 than IPM.

Scheme 3:

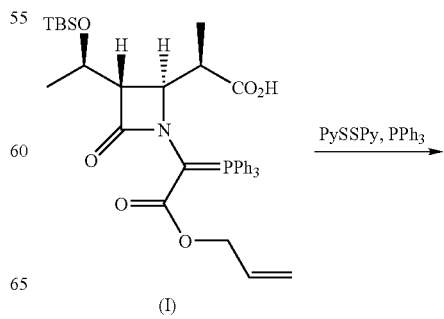

-continued

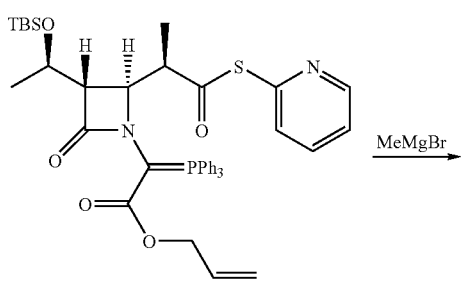

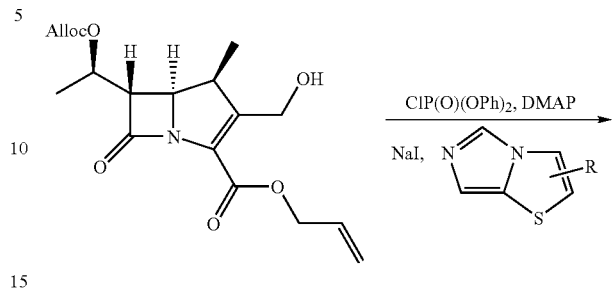

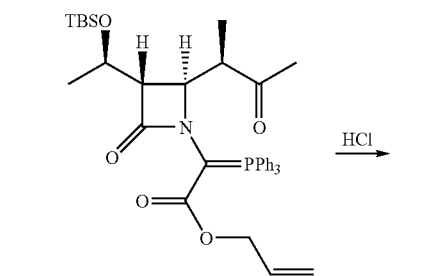

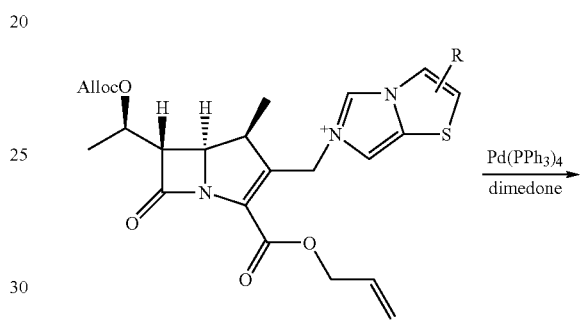

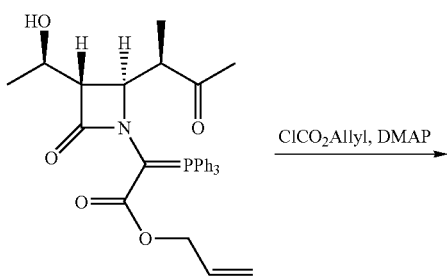

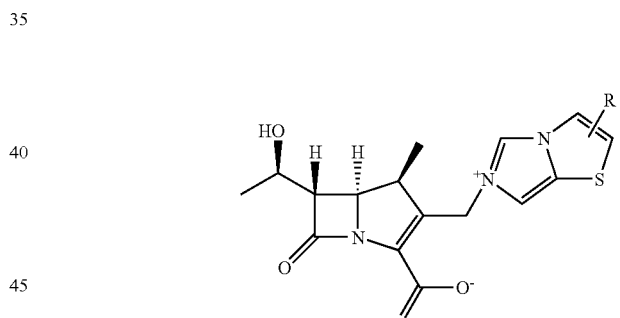

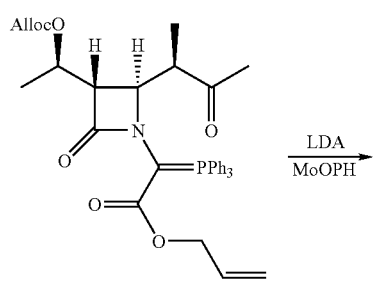

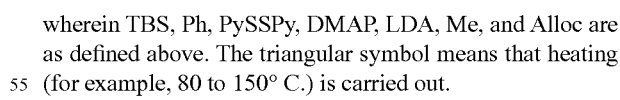

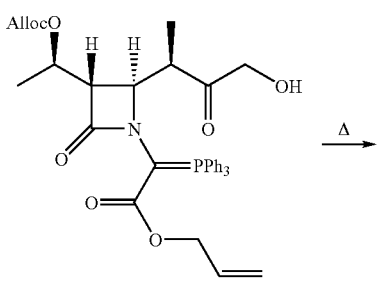

wherein TBS, Ph, PySSPy, DMAP, LDA, Me, and Alloc are as defined above. The triangular symbol means that heating (for example, 80 to 150° C.) is carried out.

WO 01/53305 describes the synthesis of 2-(7-methylthio-imidazo[5,1-b]thiazolyl)-1β-methyl carbapenem from the compound of formula (I) (see scheme 4 below). This document reports that the resultant compound has higher antimicrobial activity against *Staphylococcus aureus, Enterococcus*, pneumococci including PRSP, *Haemophilus influenzae* including ampicillin-resistant *Haemophilus influenzae, Moraxella catarrhalis* and the like than IPM and has higher stability against renal DHP-1 than IPM.

Scheme 4:
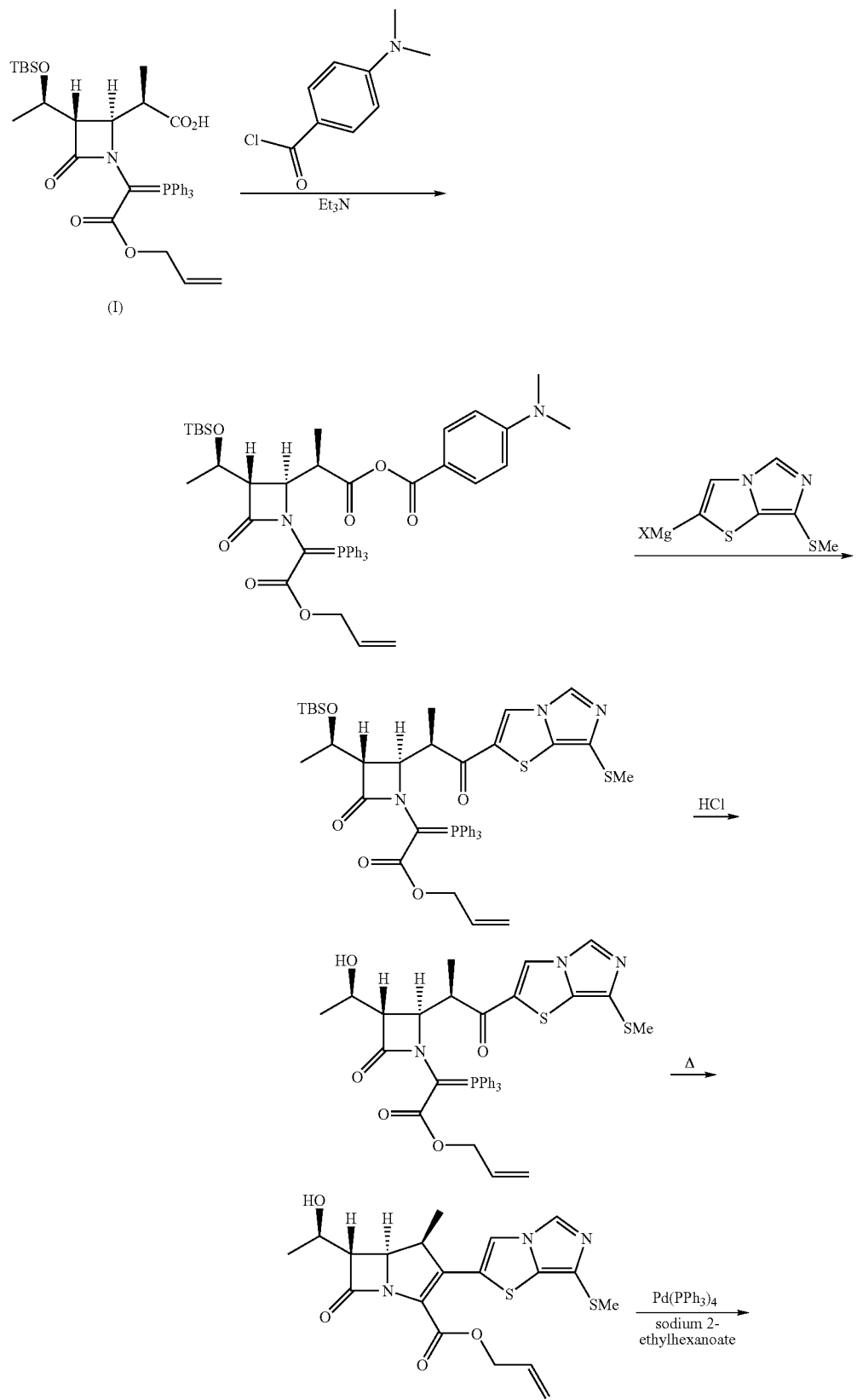

-continued

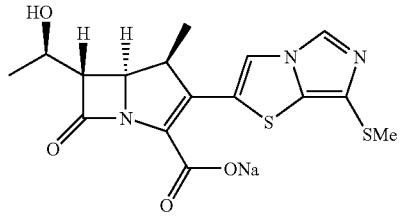

wherein TBS, Ph, and Me are as defined above; Et represents ethyl; and X represents a halogen atom. The triangular symbol means that heating (for example, 80 to 150° C.) is carried out.

The structures and synthetic processes for compounds of formula (I) are known to a person having ordinary skill in the art. However, as described, for example, in J. Med. Chem., 30, 871 (1987) (particularly page 876, right column), regarding compounds of formula (I) (corresponding to compound 16 in the above document), any crystal form was not produced although "light brown thick oils" were obtained.

In the production of contemplated carbapenem antimicrobial compounds on a commercial scale, the compound of formula (I) in the thick oil form was not easy to handle. Further, when the oil compound is purified for improving the yield of the final target compound, for example, treatment with a column using a large amount of silica gel is necessary, leading to increased cost.

Thus, compounds of formula (I) not in a crystal form have hitherto been known. So far as the present inventors know, however, crystal forms of compounds of formula (I) have not been known up to now, and even an attempt to produce such crystal form has not been made.

SUMMARY OF THE INVENTION

The present inventors have now succeeded in obtaining a crystal form of the compound of formula (I) the presence of which has not been known. Specifically, the present inventors have found that a crystal of the compound of formula (I) or its salt or solvate can be produced by carrying out a specific crystallization procedure using a specific solvent. The present invention has been made based on such finding.

Accordingly, an object of the present invention is to provide a crystal form of a compound of formula (I) which is a synthetic intermediate of a 2-substituted-1β-methyl carbapenem compound useful as antimicrobial agents.

The crystal according to the present invention is a crystal of the compound of formula (I), its salt, or their solvate:

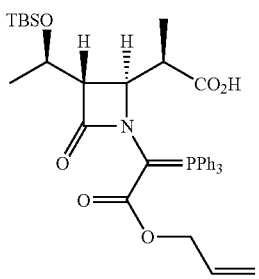

(I)

wherein TBS represents t-butyldimethylsilyl; and Ph represents phenyl.

The process for producing a crystal of a compound of formula (I) or its salt or solvate according to the present invention comprises dissolving the compound of formula (I) in a solvent selected from the group consisting of water, methanol, ethanol, propanol, isopropyl alcohol, n-butanol, diethyl ether, methyl acetate, ethyl acetate, propyl acetate, butyl acetate, and a mixture of any one of said solvents with a solvent for crystallization, and precipitating a crystal from the solution.

Further, according to the present invention, there is provided use of the crystal as a synthetic intermediate for the production of 2-substituted-1β-methyl carbapenem-based antimicrobial agent compounds.

The use of the crystal according to the present invention as a synthetic intermediate can realize the production of carbapenem compounds having high microbial activity in a simpler manner and can improve the yield of the carbapenem compounds. Further, according to the present invention, since the compound of formula (I) can be provided as a crystal form, in the production of the compound of formula (I) on a commercial scale, the synthesis, isolation, and purification of the compound of formula (I) can be facilitated and simplified. Further, the handleability of the crystal form per se is excellent. Furthermore, according to the present invention, the yield and purity of the intermediate after the production of the compound of formula (I) in the process of producing a carbapenem compound can be improved. That is, the crystal according to the present invention is favorable as a synthetic intermediate for the production of a 2-substituted-1β-methyl carbapenem compound from the viewpoints of stability and purity.

DETAILED DESCRIPTION OF THE INVENTION

Crystal According to Invention

As described above, the crystal according to the present invention is a crystal of the compound of formula (I), its salt or their solvate. The crystal according to the present invention is useful as a synthetic intermediate for the production of 2-substituted-1β-methyl carbapenem compounds.

In the present invention, the crystal refers to a solid having an internal structure comprising three-dimensionally, regularly and repeatedly ordered constituent atoms or molecules and is distinguished from an amorphous solid or a noncrystalline form free from such regularly ordered internal structure. In general, even in the case of an identical compound, crystals (crystal polymorphs) having a plurality of different internal structures and physicochemical properties are formed under some crystallization conditions. In the present invention, the crystal may be any of these crystal polymorphs or may be a mixture of two or more crystal polymorphs.

A crystal of a compound of formula (I), a crystal of a salt of a compound of formula (I), and a crystal of a solvate of a compound of formula (I) are of course embraced in the crystal according to the present invention. In addition, a crystal of a solvate of a salt of a compound of formula (I) is also embraced in the crystal according to the present invention.

In the present invention, the salt of the compound of formula (I) is not particularly limited so far as it can be derived using conventional organic acids or inorganic acids. Since, however, the final product produced using the compound of formula (I) as a synthetic intermediate may be used as an antimicrobial agent, this salt is preferably a pharmaceutically acceptable salt. The term "pharmaceutically acceptable salt" as used herein refers to a salt that is suitable for use in pharmaceutical preparation applications and is basically nontoxic to organisms. Such pharmaceutically acceptable salts include those derived from pharmaceutically acceptable inorganic or organic acids, that is, inorganic acid salts and organic acid salts. Examples of preferred acids include hydrochloric acid, sulfuric acid, nitric acid, perchloric acid, hydrobromic acid, fumaric acid, maleic acid, phosphoric acid, glycolic acid, lactic acid, salicylic acid, succinic acid, p-toluenesulfonic acid, di-p-toluoyltartaric acid, sulfanilic acid, tartaric acid, acetic acid, citric acid, methanesulfonic acid, formic acid, benzoic acid, malonic acid, naphthalene-2-sulfonic acid, and benzenesulfonic acid.

When the compound of formula (I) is placed in a solution or suspended state using a certain solvent, in some cases, the compound, together with the molecules of the solvent, forms a crystal. Likewise, when the compound of formula (I) is placed in a system in which a certain solvent is brought to a vapor form, in some cases, the compound, together with the molecules of the solvent, forms a crystal. In the present invention, this material formed by crystallization of the compound of formula (I) and the solvent in a three-dimensional order will be called a solvate. Solvents usable for solvate formation include water, alcohols, ethers, and esters. Therefore, in the present invention, the expression "solvate of the compound of formula (I) or its salt" is used in referring to embrace hydrates.

Specific examples of solvents usable for solvate formation include water, methanol, ethanol, propanol, isopropyl alcohol, n-butanol, diethyl ether, methyl acetate, ethyl acetate, propyl acetate, and butyl acetate.

In a preferred embodiment of the present invention, the crystal according to the present invention is a crystal of a compound of formula (I) or its solvate. More preferably, the crystal is a crystal of a hydrate, an alcoholate, or a solvate with an ester solvent. More preferably, the crystal is a solvate of the compound of formula (I) with an alkyl acetate solvent. The alkyl acetate refers to an ester of a C1-6 (preferably C1-4) alcohol with acetic acid and may also be expressed as C1-6 alkyl acetate or C1-6 alkyl ester of acetic acid.

In one particularly preferred embodiment of the present invention, the crystal according to the present invention is a crystal of a solvate of a compound of formula (I) with ethyl acetate, a crystal of a solvate of a compound of formula (I) with a butyl acetate, or a crystal of a solvate of a compound of formula (I) with ethyl acetate or butyl acetate and hexane.

In the present invention, that the compound of formula (I), its salt, or their solvate is in a crystal form can be confirmed by utilizing observation under a polarization microscope, a powder X-ray crystal analysis, or a single crystal X-ray diffraction measurement. The type of the crystal may also be identified by comparison of the characteristics of the crystal with data based on each index which have been previously measured. Thus, in a preferred embodiment of the present invention, the crystal according to the present invention can be identified to be a crystal by utilizing the above measuring means.

Crystal I

In a first embodiment of the present invention, there is provided a crystal of a compound of formula (I) with an ethyl acetate solvate. The crystal of a compound of formula (I) with an ethyl acetate solvate (hereinafter often referred to as "crystal I") can be produced, for example, by a method described in Example 2 which will be described later. The crystal of the ethyl acetate solvate exhibits a powder X-ray diffraction pattern described in Example 2 which will be described later. This crystal can be characterized by diffraction angles of diffraction peaks observed in the powder X-ray diffraction pattern.

Accordingly, in one preferred embodiment of the present invention, the crystal according to the present invention exhibits a powder X-ray diffraction pattern having diffraction peaks at at least diffraction angles (2θ) shown in Table I-a below:

TABLE I-a

| Diffraction angle (2θ) [°] |
|---|
| 10.2 ± 0.1 |
| 11.7 ± 0.1 |
| 17.0 ± 0.1 |
| 21.5 ± 0.1. |

As described above, this crystal is a crystal of an ethyl acetate solvate.

The powder X-ray diffraction pattern referred to herein may be determined by measurement using a measuring apparatus and measuring conditions in Example 2 which will be described later.

A more preferred embodiment of the present invention, this crystal exhibits a powder X-ray diffraction pattern having diffraction peaks at at least diffraction angles (2θ) shown in Table I-b below:

TABLE I-b

| Diffraction angle (2θ) [°] |
|---|
| 10.2 ± 0.1 |
| 11.7 ± 0.1 |
| 11.9 ± 0.1 |
| 17.0 ± 0.1 |
| 21.5 ± 0.1. |

In the present invention, some errors may be observed in diffraction angle (2θ) values due to various error sources. Error sources attributable to sample powder include particle size, water content, density, and crystallinity of sample powder, and error sources attributable to measurement environments include temperature, humidity, atmosphere, and measuring persons. Further error sources attributable to the measuring apparatus include, for example, the output of X-ray lamps, counters, various slit widths and scanning speeds. In the present specification, when the crystal is defined by diffraction angles 2θ, the diffraction angle 2θ value is not limited to the value indicated on the basis that a peak exists, and a range based on this, and the range in which errors are possibly observed may be included as the diffraction angle 2θ value in the crystal of the present invention. This range in which errors are observed can easily be predicted by a person having ordinary skill in the art from measuring conditions and the like. This is true of crystal II and crystal III which will be described later.

In the present invention, the expression "having diffraction peaks" at specific diffraction angles (2θ) in a powder X-ray diffraction pattern refers to, for example, a case satisfying the following conditions. Specifically, at specific diffraction angles, a value obtained by subtracting background (sum of noncrystalline scattering and noncoherent scattering) from absolute intensity is designated as "signal intensity." ½ of oscillation of noise at a specific diffraction angle is designated as "noise level." When the ratio between "signal intensity" and "noise level" is not less than 2, this state may be regarded as "having diffraction peaks."

Further, this crystal (crystal I) has the following crystallographic properties:

Crystal system: triclinic system
Space group: P1
Lattice constant: a: 14.582 (5) angstrom, b: 15.117 (7) angstrom, c: 25.663 (6) angstrom, α: 84.39° (3), β: 88.69° (2), γ: 89.23° (4), V: 5628 (3).

The crystallographic properties may be determined by measurement using a measuring apparatus and measuring conditions in a single crystal X-ray diffraction analysis in Example 2 which will be described later.

Accordingly, in another preferred embodiment of the present invention, the crystal (particularly crystal I) according to the present invention is characterized by at least having crystallographic properties as indicated by the above lattice constant in a single crystal X-ray diffraction analysis.

Crystal II

In a second embodiment of the present invention, there is provided a crystal of a solvate of a compound of formula (I) with butyl acetate. The crystal of a solvate of a compound of formula (I) with butyl acetate (hereinafter often referred to as "crystal II") may be produced, for example, by a process described in Example 3 which will be described later. The crystal of the butyl acetate solvate exhibits a powder X-ray diffraction pattern as described in Example 3 which will be described later. This crystal can be characterized by diffraction angles of diffraction peaks observed in the powder X-ray diffraction pattern.

Accordingly, in one preferred embodiment of the present invention, the crystal according to the present invention exhibits a powder X-ray diffraction pattern having diffraction peaks at at least diffraction angles (2θ) shown in Table II-a below:

TABLE II-a

| Diffraction angle (2θ) [°] |
| --- |
| 9.3 ± 0.1 |
| 12.5 ± 0.2 |
| 13.7 ± 0.2 |
| 15.7 ± 0.2. |

As described above, this crystal is a crystal of a butyl acetate solvate.

The powder X-ray diffraction pattern referred to herein may be determined by measurement using a measuring apparatus and measuring conditions in Example 3 which will be described later.

In one more preferred embodiment of the present invention, the crystal exhibits a powder X-ray diffraction pattern having diffraction peaks at at least diffraction angles (2θ) shown in Table II-b below:

TABLE II-b

| Diffraction angle (2θ) [°] |
| --- |
| 8.0 ± 0.1 |
| 9.3 ± 0.1 |
| 9.8 ± 0.2 |
| 12.5 ± 0.2 |
| 13.7 ± 0.2 |
| 15.7 ± 0.2. |

This crystal (crystal II) has the following crystallographic properties.

Crystal system: orthorhombic system
Space group: $P2_12_12_1$
Lattice constant: a=16.223 (7) angstroms, b=18.01 (1) angstroms, c=15.045 (7) angstroms, α=90°, β=90°, γ=90°, V=4395 (3).

The crystallographic properties may be determined by measurement using a measuring apparatus and measuring conditions in a single crystal X-ray diffraction analysis in Example 3 which will be described later.

Accordingly, in another preferred embodiment of the present invention, the crystal (particularly crystal II) according to the present invention is characterized by at least having crystallographic properties as indicated by the above lattice constant in a single crystal X-ray diffraction analysis.

Crystal III

In a third embodiment of the present invention, there is provided a crystal, different from crystal II, obtained by crystallization of a compound of formula (I) using butyl acetate (hereinafter often referred to as "crystal III"). This crystal may be produced, for example, by a process described in Example 4 which will be described later. Crystal III exhibits a powder X-ray diffraction pattern as described in Example 4 which will be described later. This crystal can be characterized by diffraction angles of diffraction peaks observed in the powder X-ray diffraction pattern.

Accordingly, in one preferred embodiment of the present invention, the crystal according to the present invention exhibits a powder X-ray diffraction pattern having diffraction peaks at at least diffraction angles (2θ) shown in Table III-a below:

TABLE III-a

| Diffraction angle (2θ) [°] |
| --- |
| 5.7 ± 0.1 |
| 11.2 ± 0.2 |
| 13.9 ± 0.2 |
| 14.5 ± 0.2. |

The powder X-ray diffraction pattern referred to herein may be determined by measurement using a measuring apparatus and measuring conditions in Example 4 which will be described later.

In one more preferred embodiment of the present invention, the crystal exhibits a powder X-ray diffraction pattern having diffraction peaks at at least diffraction angles (2θ) shown in Table III-b below:

TABLE III-b

| Diffraction angle (2θ) [°] |
| --- |
| 5.7 ± 0.1 |
| 8.4 ± 0.1 |

TABLE III-b-continued

| Diffraction angle (2θ) [°] |
| --- |
| 10.3 ± 0.1 |
| 11.2 ± 0.2 |
| 13.9 ± 0.2 |
| 14.5 ± 0.2. |

Production of Crystal of Compound

The compound of formula (I) may be produced, for example, by processes described in known documents such as J. Med. Chem., 30, 871 (1987), J. Antibiotics, 41, 780 (1988), WO 96/28455, or WO 01/53305. A specific example of the production process is to produce the compound of formula (I) by the process in Example 1 which will be described later. A salt of the compound of formula (I) may be produced by a person having ordinary skill in the art by applying conventional means to the compound of formula (I).

According to the present invention, the crystal of the compound of formula (I) may be produced by utilizing a crystallization method in which the organic solvent used in combination with the compound of formula (I) is properly selected, for example, a vapor diffusion method utilizing vapor equilibrium of the solvent, or a method utilizing concentration of a solution upon evaporation of the solvent, or saturation solubility. Crystals of the salt of the compound of formula (I), its solvate, and the solvent of the salt can be produced in the same manner as described above.

According to the present invention, there is provided a process for producing a crystal of a compound of formula (I) or its salt or solvate according to the present invention, said process comprising dissolving the compound of formula (I) in a solvent selected from the group consisting of water, methanol, ethanol, propanol, isopropyl alcohol, n-butanol, diethyl ether, methyl acetate, ethyl acetate, propyl acetate, butyl acetate, and a mixture of any one of said solvents with a solvent for crystallization, and precipitating a crystal from the solution.

The solvent for crystallization is not particularly limited so far as it can accelerate the precipitation of the crystal according to the present invention, or can lower the solubility of the crystal, and examples thereof include n-pentane, n-hexane, n-heptane, cyclohexane, petroleum ether, diisopropyl ether, and diethyl ether. n-Hexane is preferred.

In a preferred embodiment of the present invention, a solvent selected from the group consisting of ethyl acetate, butyl acetate, and a mixture composed of any one of these solvents with a solvent for crystallization is used as the solvent for dissolving the compound of formula (I).

In a preferred embodiment of the present invention, the process for producing a crystal of the compound of formula (I) or its salt or solvate comprises subjecting the above solution and a separately provided solvent for crystallization to the procedure of a vapor diffusion method to precipitate crystals. In this case, the procedure of the vapor diffusion method comprises placing the above solution and the separately provided solvent separately from each other within a hermetically sealable vessel in a volume ratio of 1:1 to 1:20, preferably 1:2 to 1:10 and allowing them to stand. Further, the crystal obtained after standing may be if necessary subjected to filtration and drying.

In a preferred embodiment of the present invention, the crystal according to the present invention may be obtained by precipitating a crystal from a solution of the compound of formula (I) dissolved in ethyl acetate.

In a more preferred embodiment of the present invention, when ethyl acetate is used as the solvent for dissolving the compound of formula (I), the resultant crystal is a crystal of a solvate of the compound of formula (I) with ethyl acetate.

In another preferred embodiment of the present invention, the crystal according to the present invention may be obtained by precipitating a crystal from a solution of the compound of formula (I) dissolved in butyl acetate or a mixture of butyl acetate with a solvent for crystallization.

In a more preferred embodiment of the present invention, when butyl acetate or a mixed solvent composed of butyl acetate and n-hexane is used as the solvent for dissolving the compound of formula (I), the resultant crystal is a crystal of a solvate of the compound of formula (I) with butyl acetate.

In a more preferred embodiment of the present invention, in the production process of the crystal, a compound obtained by dissolving a noncrystalline form of the compound of formula (I) in ethyl acetate or butyl acetate, further adding n-hexane to the solution, cooling the mixture, and vacuum drying the resultant solid matter may be used as the compound of formula (I) to be dissolved in the solvent.

The noncrystalline form of the compound of formula (I) is, for example, a compound prepared in Example 1 which will be described later.

Use of Compound

The compounds of formula (I) according to the present invention are useful as synthetic intermediates of 2-substituted-1β-methyl carbapenem compounds, for example, 2-aryl-1β-methyl carbapenem, 2-ureido-1β-methyl carbapenem, 2-imidazo[5,1-b]thiazolium methyl-1β-methyl carbapenem, and 2-(7-methylthioimidazo[5,1-b]thiazolyl-1β-methyl carbapenem, which are useful as antimicrobial agents.

As described above, 2-aryl-1β-methyl carbapenem obtained using the compound of formula (I) according to the present invention has higher antimicrobial activity against *Staphylococcus aureus, Enterococcus, Escherichia coli* and the like than imipenem (IPM) and has higher stability against renal DHP-1 than IPM, as disclosed in J. Med. Chem., 30, 871 (1987). Further, 2-ureido-1β-methyl carbapenem has higher antimicrobial activity against *Enterococcus, Escherichia coli, Klebsiella* pneumoniae and the like than IPM and higher stability against renal DHP-1 than IPM, as disclosed in J. Antibiotics, 41, 780 (1988). 2-Imidazo[5,1-b]thiazoliumm-ethyl-1β-methyl carbapenem has higher antimicrobial activity against *Staphylococcus* aureus including MRSA, *Enterococcus, Escherichia coli*, pneumococci, *Pseudomonas aeruginosa* and the like than IPM and has higher stability against renal DHP-1 than IPM, as disclosed in WO 96/28455. Further, 2-(7-methylthioimidazo[5,1-b]thiazolyl)-1β-methyl carbapenem has higher antimicrobial activity against *Staphylococcus aureus, Enterococcus*, pneumococci including PRSP, *Haemophilus influenzae* including ampicillin-resistant *Haemophilus influenzae, Moraxella catarrhalis* and the like than IPM and has higher stability against renal DHP-1 than IPM, as disclosed in WO 01/53305. The use of these compounds as a therapeutic agent for infectious diseases attributable to various pathogenic bacteria of animals including humans and the production of pharmaceutical compositions using these compounds will be apparent to a person having ordinary skill in the art by reference to the above documents.

Further, a production process of an antimicrobial carbapenem compound using the crystal according to the present invention as a synthetic intermediate is apparent, for example, from the above documents (J. Med. Chem., 30, 871 (1987), J. Antibiotics, 41, 780 (1988), WO 96/28455, or WO 01/53305), more specifically apparent from the above-described schemes 1 to 4.

EXAMPLES

The present invention is further illustrated by the following Examples that are not intended as a limitation of the scope of the invention.

Example 1

Synthesis of Compound of Formula (I)

(3S,4S)-3-[(1R)-1-(t-Butyldimethylsilyloxy)ethyl]-4-[(1R)-1-carboxyethyl]-2-azetidinone used was a commercially available one (for example, available from Kanefuchi Chemical Co, Ltd., NIPPON SODA CO., LTD., or Takasago International Corp.).

t-Butyldimethylsilyl chloride (49.74 g, 0.33 mol) and imidazole (22.47 g, 0.33 mol) were continuously added to a solution of (3S,4S)-3-[(1R)-1-(t-butyldimethylsilyloxy)ethyl]-4-[(1R)-1-carboxyethyl]-2-azetidinone (90.4 g, 0.30 mol) in 450 mL of dry N,N-dimethylformamide (DMF). The mixture was then stirred in an argon atmosphere at 50° C. for 4 hr. Next, the solution thus obtained was removed by evaporation under the reduced pressure at a bath temperature of 30° C. The residue was dissolved in 1.5 L of petroleum ether and was washed with 0.4 L of water, followed by extraction with 0.4 L of petroleum ether from the aqueous phase. The organic phases were combined. The organic phase was washed with 0.33 L of cold 1 N hydrochloric acid, cold 5% sodium bicarbonate water (0.5 L×2), and 0.4 L of saturated brine in a successive manner and was dried over anhydrous magnesium sulfate. Thereafter, the organic layer was filtered, and the solvent was removed by evaporation under the reduced pressure to give a solid of a t-butyldimethylsilyl (TBS) ester compound (117.6 g, yield 94.3%).

Allyl glyoxylate monohydrate (42.9 g, 0.325 mol) was added to a solution of 102.9 g (0.25 mol) of the TBS ester compound dissolved in 1.25 L of dry toluene. While removing water being produced with a Dean-Stark device, the mixture was heated under reflux for 10 hr. Thereafter, the solvent was removed by evaporation under the reduced pressure. The thick material thus obtained was dissolved in 0.8 L of dry tetrahydrofuran. The solution was cooled to −40° C. Thereafter, 2,6-lutidine (48.2 g, 0.45 mol) and thionyl chloride (53.5 g, 0.45 mol) were continuously added dropwise at an internal temperature of −25° C. or below. Thereafter, the mixture was stirred at −20° C. for 1.5 hr, and the insolubles were then removed by filtration. The solvent was removed from the filtrate by evaporation under the reduced pressure. Thereafter, 1 L of dry ethyl acetate was added to the residue, and the insolubles were removed by filtration. The solvent was removed from the filtrate, by evaporation under the reduced pressure. The brown oil thus obtained was dissolved in 0.35 L of DMF, triphenylphosphine (118 g, 0.45 mol) was added to the solution, and the mixture was stirred at room temperature overnight. The solvent was removed by evaporation under the reduced pressure, 1.5 L of ethyl acetate was then dissolved in the residue, and the solution was washed with 0.25 M phosphate buffer (pH 6.9) (1 L×2) and 1 L of saturated brine in that order. Next, the solution thus obtained was dried over anhydrous magnesium sulfate and was filtered. The solvent was removed from the filtrate by evaporation under the reduced pressure to give a brown oil. The brown oil was purified by column chromatography on silica gel (1.5 kg of Silica Gel 60 (spherical)), manufactured by KANTO CHEMICAL CO., INC., chloroform:ethyl acetate=5:1) to give a compound of formula (I) (99.3 g, yield 71.7%) as a light yellow thick material (noncrystalline material).

Example 2

Crystal I 2-a) Crystallization of Compound of Formula (I)

A part of the light yellow thick material obtained above was further purified by column chromatography on silica gel (Wako Gel C-300, manufactured by Wako Pure Chemical Industries, Ltd., n-hexane:ethyl acetate=1:1), and the solvent was removed by evaporation. The crude product thus obtained was dissolved in a minor amount of ethyl acetate, and n-hexane was added to the solution to give a crude crystal of the compound of formula (I).

Ethyl acetate (2.9 L) was added to 1.367 kg of the crude crystal of the compound of formula (I), and the mixture was heated to 40° C. with stirring for dissolution. Thereafter, 3.9 L of n-hexane was gradually added to the solution. When crystals began to precipitate, the system was dipped in an iced water bath, and ripening was carried out with slow stirring overnight. The crystals were collected through a glass filter and were washed with 1 L of n-hexane, and this washing was repeated three times. Next, the crystals were vacuum dried at a shelf temperature of 30° C. overnight to give 1.232 kg of colorless crystals of the compound of formula (I).

NMR (CDCl$_3$) δ: −0.14 (3H, s), −0.07 (3H, s), 0.81 (9H, s), 0.98 (3H, d, J=6.0 Hz), 1.14 (3H, d, J=7.1 Hz), 2.26-2.36 (1H, m), 2.60-2.69 (2H, m), 3.12-3.20 (1H, m), 4.15-4.29 (2H, m), 4.60-4.76 (2H, m), 5.10-5.24 (1H, m), 7.50-7.57 (6H, m), 7.61-7.68 (3H, m), 7.71-7.79 (6H, m) MS (SIMS):m/z=660 (M$^+$+1)

2-b) Preparation of Crystal by Vapor Diffusion

The crystal (2.5 g) of the compound of formula (I) synthesized according to Example 2-a) was placed in a 20 mL beaker, and 15 mL of ethyl acetate was added thereto to dissolve the crystal. The 20 mL beaker containing the ethyl acetate solution of the crude crystal was placed in an opened state within a 300 mL beaker containing 50 mL of n-hexane. The opening of the 300 mL beaker was covered with an aluminum foil, and the beaker was allowed to stand at room temperature (about 25° C.) for 4 days. The solid matter thus obtained was collected by filtration and was dried to give a colorless platy crystal (crystal I).

This crystal was considered to be an ethyl acetate solvate of the compound of formula (I).

2-c) Powder X-Ray Diffraction Measurement

For the crystal (crystal I) obtained in the above 2-b), powder X-ray diffraction measurement was carried out using the following apparatus under the following measuring conditions.

Apparatus: RINT 2100 (manufactured by Rigaku Industrial Corporation)

Measuring conditions: X-ray: CuKα$_1$, tube voltage: 40 kV, tube current: 40 mA, scan step: 0.02°, scan speed: 4°/min, scanning axis: 2θ/θ, and scan range: 2θ=3 to 40°

The results were as follows.

The above crystal had characteristic diffraction peaks at the following diffraction angle (2θ).

| Diffraction angle (2θ) [°] |
| --- |
| 10.2 ± 0.1 |
| 11.7 ± 0.1 |
| 11.9 ± 0.1 |
| 17.0 ± 0.1 |
| 21.5 ± 0.1 |

2-d) Single Crystal X-Ray Diffraction Measurement

For the crystal (crystal I) obtained in the above 2-b), single crystal X-ray diffraction measurement was carried out using the following apparatus under the following measuring conditions.

Apparatus: RIGAKU AFC-7R (manufactured by Rigaku Industrial Corporation)

Measuring conditions: X-ray: CuKα, tube voltage: 50 kV, tube current: 90 mA, and measuring temperature: −180° C.

As a result of the measurement, the crystal had the following crystallographic properties.

Crystal system: triclinic system

Space group: P1

Lattice constant: a: 14.582 (5) angstrom, b: 15.117 (7) angstrom, c: 25.663 (6) angstrom, α: 84.39° (3), β: 88.69° (2), γ: 89.23° (4), V: 5628 (3).

Example 3

Crystal II 3-a) Preparation of Crystal by Vapor Diffusion

The crystal (1.66 g) of the compound of formula (I) synthesized according to Example 2-a) was placed in a 50 mL beaker, and 10 mL of butyl acetate was added thereto to dissolve the crystal. Further, 0.2 mL of n-hexane was added to the solution. A 50 mL beaker containing a mixed solution prepared by dissolving the crude crystal in butyl acetate and n-hexane was placed in an opened state within a 500 mL beaker containing 100 mL of n-hexane. The opening of the 500 mL beaker was covered with an aluminum foil, and the beaker was allowed to stand at room temperature (about 25° C.) for one day. The solid matter thus obtained was collected by filtration and was dried to give a colorless prismatic crystal (crystal II).

This crystal was considered to be a butyl acetate solvate of the compound of formula (I).

3-b) Powder X-Ray Diffraction Measurement

For the crystal (crystal II) obtained in the above 3-a), powder X-ray diffraction measurement was carried out using the following apparatus under the following measuring conditions.

Apparatus: RINT 2100 (manufactured by Rigaku Industrial Corporation)

Measuring conditions: X-ray: CuKα$_1$, tube voltage: 40 kV, tube current: 20 mA, scan step: 0.02°, scan speed: 4°/min, scanning axis: 2θ/θ, and scan range: 2θ=3 to 40°

The results were as follows.

The above crystal had characteristic diffraction peaks at the following diffraction angle (2θ).

| Diffraction angle (2θ) [°] |
| --- |
| 8.0 ± 0.1 |
| 9.3 ± 0.1 |
| 9.8 ± 0.2 |
| 12.5 ± 0.2 |
| 13.7 ± 0.2 |
| 15.7 ± 0.2 |

3-c) Single Crystal X-Ray Diffraction Measurement

For the crystal (crystal II) obtained in the above 3-a), single crystal X-ray diffraction measurement was carried out using the following apparatus under the following measuring conditions.

Apparatus: RIGAKU AFC-7R (manufactured by Rigaku Industrial Corporation)

Measuring conditions: X-ray: CuKα, tube voltage: 50 kV, tube current: 85 mA, and measuring temperature: −160° C.

As a result of the measurement, the crystal had the following crystallographic properties.

Crystal system: triclinic system

Space group: P1

Lattice constant: a: 14.582 (5) angstrom, b: 15.117 (7) angstrom, C: 25.663 (6) angstrom, α: 84.39° (3), β: 88.69° (2), γ: 89.23° (4), V: 5628 (3).

Example 4

Crystal III 4-a) Preparation of Crystal (1)

Butyl acetate (3.8 mL) was added to 1.22 g of the crude crystal of the compound of formula (I) synthesized according to Example 1, the mixture was heated to 60° C. to dissolve the crystal, and 1.6 mL of n-hexane was further added to the solution. The solution was stirred at room temperature for one hr, and the precipitated crystal was then collected by filtration and was washed with a mixed solution composed of butyl acetate and n-hexane (2:1), followed by vacuum drying for 7 hr to give 630 mg of a colorless crystal (crystal III).

4-b) Preparation of Crystal (2)

Butyl acetate (2.4 mL) was added to 1.21 g of the crude crystal of the compound of formula (I) synthesized according to Example 1, the mixture was heated to 60° C. to dissolve the crystal, and the solution was allowed to stand at room temperature for 1.5 hr. The solution was further cooled on a water bath for one hr, and the precipitated crystal was then collected by filtration and was washed with a mixed solution composed of butyl acetate and n-hexane (2:1), followed by vacuum drying for 4 hr to give 739 mg of a colorless crystal (crystal III).

4-c) Powder X-Ray Diffraction Measurement

For the crystal (crystal III) obtained in the above 4-a), powder X-ray diffraction measurement was carried out using the following apparatus under the following measuring conditions.

Apparatus: RINT 2100 (manufactured by Rigaku Industrial Corporation)

Measuring conditions: X-ray: CuKα$_1$, tube voltage: 40 kV, tube current: 20 mA, scan step: 0.02°, scan speed: 4°/min, scanning axis: 2θ/θ, and scan range: 2θ=3 to 40°

The results were as follows.

The above crystal had characteristic diffraction peaks at the following diffraction angle (2θ).

| Diffraction angle (2θ) [°] |
| --- |
| 5.7 ± 0.1 |
| 8.4 ± 0.1 |
| 10.3 ± 0.1 |
| 11.2 ± 0.2 |
| 13.9 ± 0.2 |
| 14.5 ± 0.2 |

Evaluation Test

The above-described scheme 4 described in WO 01/53305 was actually studied as an example of the production of a carbapenem compound as a final product using the compound of formula (I) as a synthetic intermediate. In particular, attention was drawn to the first step of scheme 4, that is, the step of producing a compound in the second-stage compound in scheme 4 (compound of formula (II)) using the compound of formula (I) (the following scheme 5), and the following test was carried out.

In the test, a crystal form of the compound of formula (I) and a noncrystalline form of the compound of formula (I) were used as starting compounds to produce the compound of formula (II) according to scheme 5. The crystal form of the compound of formula (I) was the compound (crystal I) prepared according to Example 2, and the noncrystalline form of the compound of formula (I) was the compound prepared according to Example 1.

Scheme 5:

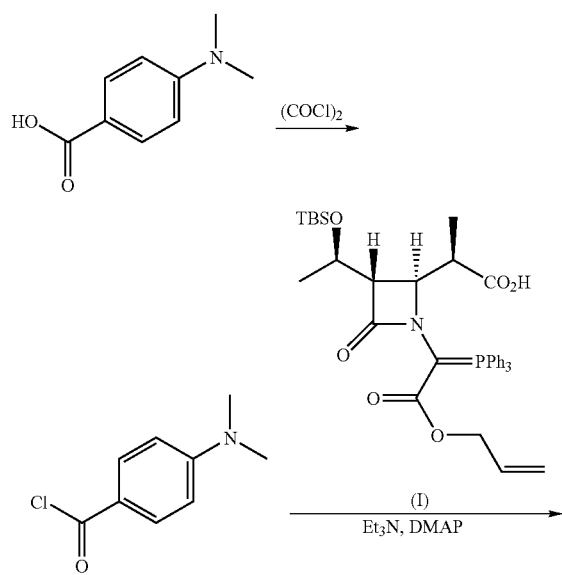

-continued

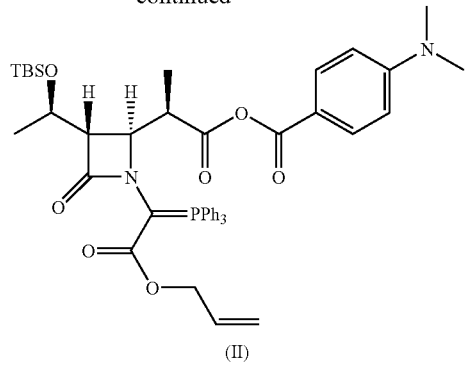

wherein TBS, Ph, and DMAP are as defined above.

Test 1: Case where Noncrystalline form of Compound of Formula (I) was used (Comparative Example)

Oxalyl chloride (375 g) was added to a suspension prepared by adding 3.0 L of dry methylene chloride to 371.7 g of N,N-dimethylaminobenzoic acid. A vessel containing the resultant solution was dipped in an oil bath, and the solution was stirred for 3 hr while controlling the internal temperature at about 40° C. The solvent was removed by evaporation under the reduced pressure, and the residue was vacuum dried to give a crude product of N,N-dimethylaminobenzoic acid chloride.

A solution of the compound of formula (I) (noncrystalline form) (1.338 kg) dissolved in 3.1 L of dry methylene chloride was added to a solution of this crude product was dissolved in 3.1 L of dry methylene chloride. Next, 12.5 g of 4-N,N-dimethylaminopyridine and 526 g of triethylamine were added to this solution, and the mixture was stirred at room temperature for 1.5 hr. The solution was diluted with 10.8 L of methylene chloride, and the diluted solution was then washed with 5.4 L of 25% brine, a mixed solution composed of 2.7 L of 1 N hydrochloric acid and 2.7 L of 25% brine, a mixed solution composed of 0.4 L of 1 N hydrochloric acid and 5.4 L of 25% of brine, and a mixed solution composed of 0.21 L of a 1 N aqueous sodium hydroxide solution and 5.4 L of 25% brine in a successive manner. Thereafter, 510 g of anhydrous magnesium sulfate was added thereto for drying, followed by filtration. The solvent in the filtrate was removed by evaporation under the reduced pressure to give 1.729 kg of a contemplated mixed acid anhydride (compound of formula (II)) (yield 78.0%, purity 74.5%).

Test 2: Case where Crystal form of Compound of Formula (I) was used (Present Invention)

Oxalyl chloride (371 g) was added to a suspension prepared by adding 3.6 L of dry methylene chloride to 358 g of N,N-dimethylaminobenzoic acid. A vessel containing the resultant solution was dipped in an oil bath, and the solution was stirred for 2.5 hr while controlling the internal temperature at about 40° C. The solvent was removed by evaporation under the reduced pressure, and the residue was vacuum dried to give a crude product of N,N-dimethylaminobenzoic acid chloride.

A solution of the compound of formula (I) (crystal form) (1.222 kg) dissolved in 2.4 L of dry methylene chloride was added to a solution of this crude product dissolved in 3.3 L of dry methylene chloride. Next, 12 g of 4-N,N-dimethylaminopyridine and 461 g of triethylamine were added to this solution, and the mixture was stirred at room temperature for 0.5 hr. The solution was diluted with 10.4 L of methylene chloride, and the diluted solution was then washed with 5.2 L of 25% brine, a mixed solution composed of 7.1 L of 1 N hydrochloric acid and 2.6 L of 25% brine, and a mixed solution composed of 0.65 L of a 1N aqueous sodium hydroxide solution and 5.2 L of 25% brine in a successive manner. Thereafter, 382 g of anhydrous magnesium sulfate was added thereto for drying, followed by filtration. The solvent in the filtrate was removed by evaporation under the reduced pressure to give 1.545 kg of a contemplated mixed acid anhydride (compound of formula (II)) (yield 93.0%, purity 90.0%).

Comparison of the results of test 1 with the results of test 2 shows that, as compared with the use of the noncrystalline form of the compound of formula (I), the use of the crystal form of the compound of formula (I) could apparently improve the yield and purity of the compound of formula (II).

This application claims priority to JP 2003-172723 filed Jun. 18, 2003. The entire contents of the above-identified application is hereby incorporated by reference.

The invention claimed is:

1. A crystal of a solvate of a compound of formula (I):

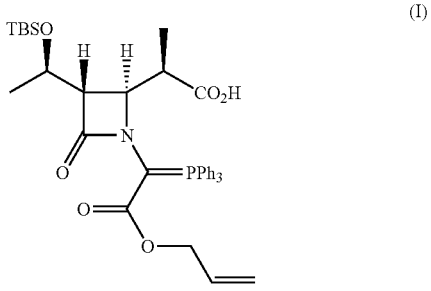

wherein TBS represents t-butyldimethylsilyl and Ph represents phenyl and the solvate is a hydrate, an alcoholate, an etherate or a solvate with an ester solvent.

2. The crystal according to claim 1, which is a crystal of an alkyl acetate solvate of the compound of formula (I).

3. The crystal according to claim 1, which is a crystal of an ethyl acetate solvate of the compound of formula (I).

4. The crystal according to claim 1, comprising a powder X ray diffraction pattern having peaks at 10.2±0.1, 11.7±0.1, 17.0±0.1 and 21.5±0.1 degrees 2θ when measured using CuKα radiation.

5. The crystal according to claim 4, comprising a powder X ray diffraction pattern having peaks at 10.2±0.1, 11.7±0.1, 11.9±0.1 17.0±0.1 and 21.5±0.1 degrees 2θ when measured using CuKα radiation.

6. The crystal according to claim 1, which can be obtained by precipitating a crystal from a solution of the compound of formula (I) dissolved in ethyl acetate.

7. The crystal according to claim 1, which is a crystal of a butyl acetate solvate of the compound of formula (I).

8. The crystal according to claim 1, comprising a powder X ray diffraction pattern having peaks at 9.3±0.1, 12.5±0.2, 13.7±0.2 and 15.7±0.2 degrees 2θ when measured using CuKα radiation.

9. The crystal according to claim 8, comprising a powder X ray diffraction pattern having peaks at 8.0±0.1, 9.3±0.1, 9.8±0.2, 12.5±0.2, 13.7±0.2 and 15.7 0.2 degrees 2θ when measured using CuKα radiation.

10. The crystal according to claim 1, comprising a powder X ray diffraction pattern having peaks at 5.7±0.1, 11.2±0.2, 13.9±0.2 and 14.5±0.2 degrees 2θ when measured using CuKα radiation.

11. The crystal according to claim 10, comprising a powder X ray diffraction pattern having peaks at 5.7±0.1, 8.4±0.1, 10.3±0.1, 11.2±0.2, 13.9±0.2 and 14.5±0.2 degrees 2θ when measured using CuKα radiation.

12. The crystal according to claim 1, obtained by precipitating a crystal from a solution of the compound of formula (I) dissolved in butyl acetate or a mixture of butyl acetate with a solvent for crystallization.

13. The crystal according to claim 12, wherein said solvent for crystallization is n-hexane or n-heptane.

14. The crystal according to claim 1, obtained by dissolving the compound of formula (I) in a solvent selected from the group consisting of water, methanol, ethanol, propanol, isopropyl alcohol, n-butanol, diethyl ether, methyl acetate, propyl acetate, butyl acetate, and a mixture of any one of said solvents with a solvent for crystallization, and precipitating a crystal from the solution.

15. A process for producing a crystal according to claim 1, said process comprising dissolving the compound of formula (I) in a solvent selected from the group consisting of water, methanol, ethanol, propanol, isopropyl alcohol, n-butanol, diethyl ether, methyl acetate, propyl acetate, butyl acetate, and a mixture of any one of said solvents with a solvent for crystallization, and precipitating a crystal from the solution.

16. The process according to claim 15, wherein said solution and a separately provided solvent for crystallization are subjected to the procedure by a vapor diffusion method to precipitate a crystal.

17. The process according to claim 16, wherein said procedure by the vapor diffusion method comprises allowing said solution and a separately provided solvent for crystallization to stand separately in respective hermetically sealable vessels in a volume ration of 1:1 to 1:20.

18. The process according to claim 15, wherein said solvent for dissolving the compound of formula (I) is selected from the group consisting of ethyl acetate, butyl acetate, and a mixture of any one of said solvents with a solvent for crystallization.

19. The process according to claim 15, wherein said solvent for crystallization is selected from the group consisting of n-pentane, n-hexane, n-heptane, cyclohexane, petroleum ether, diisopropyl ether, and diethyl ether.

20. The process according to claim 19, wherein said solvent for crystallization is n-hexane or n-heptane.

21. The process according to claim 15, comprising dissolving a non-crystalline solid compound of formula (I) in said solvent in ethyl acetate or butyl acetate, adding n-hexane or n-heptane, cooling the mixture, and optionally isolating and drying the resultant solid matter.

* * * * *